United States Patent [19]
Duan et al.

[11] Patent Number: 5,885,592
[45] Date of Patent: Mar. 23, 1999

[54] METHODS AND PHARMACEUTICAL COMPOSITIONS FOR ORAL DELIVERY OF MOLECULAR IODINE

[75] Inventors: Yongjun Duan, Lexington; John Hickey, Marlborough; Rick Panicucci, Bedford; Jack Kessler, Southborough, all of Mass.

[73] Assignee: Symbollon Corporation, Framingham, Mass.

[21] Appl. No.: 960,149

[22] Filed: Oct. 29, 1997

[51] Int. Cl.$^6$ ..................................................... A61K 9/00
[52] U.S. Cl. .................. 424/400; 424/406; 424/438; 424/439; 424/442; 424/464; 424/479; 424/484; 424/488; 424/667
[58] Field of Search ........................ 426/2, 74; 424/405, 424/406, 438, 439, 442, 464, 476–482, 484, 485, 488, 667–672, 400

[56] References Cited

U.S. PATENT DOCUMENTS

| | | | |
|---|---|---|---|
| 4,187,294 | 2/1980 | Ishikawa et al. | 424/150 |
| 4,259,322 | 3/1981 | Lim | 424/150 |
| 4,338,304 | 7/1982 | Kamimae et al. | 424/150 |
| 4,394,376 | 7/1983 | Kamimae et al. | 424/150 |
| 4,816,255 | 3/1989 | Ghent et al. | 424/150 |
| 5,171,582 | 12/1992 | Ghent et al. | 424/667 |
| 5,250,304 | 10/1993 | Ghent et al. | 424/667 |
| 5,389,385 | 2/1995 | Ghent et al. | 424/667 |
| 5,589,198 | 12/1996 | Eskin et al. | 424/667 |

OTHER PUBLICATIONS

IAMS: Guide to Complete Nutrition Cats, Oct. 1993.
Morrison Feeds & Feeding pp. 120, 121, 1954.
"Different Tissue Responses . . . " B.A. Eskin et al, Humana Press, vol. 49, 1995, pp. 9–19.
"Distribution of Iodine . . . " K.D. Thrall et al, Jour. of Toxicology & Environmental Health, 1992, pp. 443–449.
"On tHETreatment of Dyshormonal . . . ", V.V. Vishnyakova et al, Academy of Medical Sciences USSR, pp. 26–31.
"A Review of Iodine Toxicity . . . " J.A.T. Pennington, Journal of Am. Dietetic Assn., Nov. 1990, vol. 90, No. 11 pp. 1571–1581.
"Comparison of Toxoxity . . . " T.T. Sherer et al, Jour. of Toxicology . . . 1991, pp. 89–101.
"Different Toxicological Properties of Iodine . . . " K.D. Thrall, 1990, pp. 88–94.

*Primary Examiner*—Neil S. Levy
*Attorney, Agent, or Firm*—Eugene Lieberstein; Michael N. Meller

[57] ABSTRACT

The invention is a method of administering therapeutic iodine for treating a disorder in a mammal. The invention comprises a step of feeding said mammal an effective amount of an oxidant for an iodine species and an iodine reductant which will cause oxidation-reduction reactions upon contact with the gastric juices present in the stomach of the mammal. This is done such that molecular iodine is generated in vivo at a ratio of molecular iodine to total iodine of above at least about 0.65. The invention also discloses a non-aqueous pharmaceutically acceptable carrier with said oxidant and reductant having the ability to cause oxidation-reduction reactions upon contact with the gastric juices present in the stomach of said mammal and in an amount sufficient to generate molecular iodine, in vivo, at a ratio of molecular iodine to total iodine of above at least about 0.65.

28 Claims, 1 Drawing Sheet

METHODS AND PHARMACEUTICAL COMPOSITIONS FOR ORAL DELIVERY OF MOLECULAR IODINE

FIELD OF THE INVENTION

This invention relates to a method for generating molecular iodine, in situ, in the stomach of a preferably mammal for use as an effective therapeutic such as in the treatment of fibrocystic breast syndrome as well as other diseases that require either chronic or acute dosing of therapeutic iodine at a controlled ratio of molecular iodine to total iodine of above at least 0.65 and preferably between 0.80 and 1.0 and most preferably between 0.9 and 1.0. The present invention also relates to a non aqueous pharmaceutical composition which can be orally administered to a mammal to produce an effective iodine therapeutic that has a ratio of molecular iodine to total iodine of at least 0.65 upon contact with the gastric juices in the stomach of a mammal. The method and oral pharmaceutical compositions of the present invention generate molecular iodine internally only upon contact with the gastric juices in the stomach of a mammal and at a pharmaceutically acceptable dosage in a ratio of molecular iodine to total iodine above at least 0.65.

BACKGROUND

Iodine, including organically bound iodine, inorganic iodine and molecular iodine, i.e. $I_2$, has been used to treat human diseases. Iodine-containing compounds have been employed extensively as expectorants. U.S. Pat. Nos. 4,187,294; 4,338,304 and 4,394,376 disclose compositions containing protein-bound iodine for the treatment of hypercholesteremia, diabetes and hyperlipemia. U.S. Pat. No. 4,259,322 discloses tuberculosis medication containing sodium iodide. Most recently, U.S. Pat. Nos. 4,816,255; 5,171,582; 5,250,304 and 5,389,385 disclose compositions of "elemental iodine" ($I_2$) in water for oral administration in humans to treat a variety of human diseases. U.S. Pat. No. 5,589,198 discloses the benefits of using elemental iodine or "iodine metal" with pharmaceutically acceptable carriers in the treatment of fibrocystic breast syndrome.

Much of the prior art literature refers to "iodine" in an imprecise manner. The word iodine has been used in the literature to refer to several distinct chemical species that contain iodine atoms. Many different compounds with distinct and materially different properties contain iodine. For example, the literature on iodine disinfection clearly shows that the biocidal efficacy of diverse iodine species is profoundly different; molecular iodine ($I_2$) is an active biocide while iodide ($I^-$) has no biocidal activity. Traditional beliefs in the field of toxicology (R. C. Haynes Jr and F. Murad, "Thyroid and Antithyroid Drugs" in *Goodman and Gilman's the Pharmacological Basis of Therapeutics*, Eds. A. G. Gilman et al., $7^{th}$ ed., pp. 682–815, 1985, W. B. Saunders, Philadelphia) have held that molecular iodine and iodide have identical toxicity profiles; however, no direct experimental data was used to support this assumption. In fact, the toxicity and therapeutic efficacy of these different species of iodine could vary dramatically just as their biocidal activity does. Unfortunately, the pharmaceutical literature on iodine has not drawn distinctions between the properties of the many different chemical species that contain iodine atoms.

The most serious concern for administration of an iodine pharmaceutical relates to the potential for toxic reactions. In this regard, it is believed that iodide is the form of iodine responsible for "iodide poisoning" or "iodism." There is no way of predicting which patient will react unfavorably to iodide, and an individual may vary in their sensitivity to iodide from time to time. A series of symptoms can result from iodism. Symptoms can include burning in the mouth and throat; soreness of the teeth and gum; increased salivation; coryza, irritation of the respiratory tract; cough; headache; enlarged glands; inflammation of the pharynx, larynx and tonsils; skin lesions; gastric irritation; diarrhea; fever; anorexia and depression; and severe and sometimes fatal eruptions (ioderma) may occur. In essence, human consumption of iodide at levels in excess of the range (0.150 to 1.0 mg/day) established by FDA researchers (J. A. Pennington, "A review of iodine toxicity reports", *J. Am. Dietetic Assoc.*, Vol. 90, pp. 1571–1581) presents a health risk.

The only scientific studies on the relative oral toxicity of molecular iodine and iodide was performed during the early 1990s (Karla Thrall, Ph.D. Thesis, "Formation of Organic By-Products Following Consumption of Iodine Disinfected Drinking Water", Summary and Conclusion Section, Oregon State University, Department of Chemistry, 1992). The weight of a mammals thyroid is one key diagnostic measure used to evaluate the toxicity of an iodine composition. Subchronic administration of iodide to male rats increased their thyroid weight at an iodide concentration of 10 mg/kg; molecular iodine did not effect thyroid weight even at concentrations of 100 mg/kg (Sherer et al., *Journal of Toxicology and Environmental Health*, Vol. 32, pp. 89–101, 1991). This study by Sherer did not measure an increase in the steady state levels of thyroid hormones until animals were exposed to repeated daily doses of molecular iodine at 10 mg per kilogram of body weight. It can be concluded from these studies that iodide can effect thyroid weight in mammals at concentrations that are 10 fold less than a comparable effect from molecular iodine. Another way to state this is that it required ten time more molecular iodine than iodide to effect animal thyroid function with an orally administered iodine composition.

The human body contains approximately 18 to 20 mg of iodine. Iodine is an essential component of thyroxine and tri-iodothyronine. These hormones are essential for the maintenance of normal metabolic activity and they have an effect on almost every mammalian tissue. Excess iodine can lead to an imbalance in thyroid hormones. The reduced toxicity on the thyroid gland exhibited by molecular iodine as compared to iodide in the studies by Sherer et al. has important implications for design of an oral iodine pharmaceutical. These studies indicate that, all other factors being equal, molecular iodine is a preferred form of iodine for an oral drug. This would be especially true for disease states that require chronic administrations of said iodine pharmaceutical.

An early observation of the association of thyroid/iodine with the human female breast was made in 1896, by Dr. Beatson, who treated metastatic breast cancer using desiccated thyroid in large doses. Desiccated thyroid contains an abundance of protein-bound iodine. An early association of an iodine deficiency state and benign breast dysplasia was reported in 1966 by a clinician who reported a 71% improvement rate in women with dysplastic mastodynia treated with iodine (Vishnyakova V. V. et al., "On the Treatment of Dyshormonal Hyperplasia of Mammary Glands", *Vestin. Sakad. Med. Mauk. S.S.S.R.*, Vol. 21:p. 19, 1966). Treatment of mammary dysplasia using traditional Chinese medicines like Sargassum, which contains a high iodide concentration, has provided cure rates of 65.4 percent. Ghent (U.S. Pat. Nos. 5,389,385 and 5,589,198) explored the use of elemental iodine treat a variety of human diseases. The scientific literature provides clear evidence that iodine in several different forms is an effective therapeutic against many different mammalian diseases.

Animal models of fibrocystic breast syndrome have been studies for over 40 years. Several studies provide evidence that indicates iodine can reverse this condition. Studies in humans have shown improvement or complete elimination of fibrocystic breast syndrome after several months of iodine therapy. Other mammalian disease states that have been treated with iodine include ovarian cysts, premenstrual syndrome, breast cancer and endometriosis.

For convenience, certain terms employed in the specification, examples, and appended claims are defined below.

The term "molecular iodine" as used herein, refers to diatomic iodine, which is represented by the chemical symbol $I_2$, which exists in a liquid.

The term "elemental iodine" as used herein, refers to solid diatomic iodine, which is represented by the chemical symbol $I_2$.

The term "iodide" or "iodide anion" refers to the species which is represented by the chemical symbol $I^{31}$. Suitable counter-ions for the iodide anion include sodium, potassium, calcium, and the like.

The term "triiodide" refers to the species which is represented by the chemical symbol $I_3^-$. It is recognized by one skilled in the art that triiodide is formed from the interaction of one iodide anion and one molecule of molecular iodine under the laws of mass action and that triiodide rapidly dissociates into one iodide anion and one molecule of molecular iodine.

The term "total iodine" as used herein, refers to the following iodine species: molecular iodine, iodide, organically complexed forms of iodine, covalently bound forms of iodine, iodite, triiodide, polyiodides containing more than 5 atoms of iodine and elemental iodine.

The term "rate of iodine generation" as used herein, refers to the rate at which molecular iodine is formed in a liquid environment.

The term "ratio of molecular iodine" as used herein, refers to the ratio of molecular iodine ($I_2$) to all other iodine species such as iodide, triiodide and polyiodides containing more than 5 atoms of iodine or total iodine.

Elemental iodine is sold commercially as blue-black crystals with a high metallic luster. The major difficulty with the preparation of a suitable oral composition of molecular iodine is related to the basic physical chemistry of this element. All solid forms of elemental iodine sublime readily to generate a violet-colored vapor. In fact, atmospheric iodine is a major component of global iodine cycling. Unfortunately, the facile sublimation of elemental iodine introduces an inherent instability which precludes its use, per se, as the active ingredients in a pharmaceutical preparation. Other chemicals are combined in some form with elemental iodine in order to provide stable preparations that contain molecular iodine. There are three different types or categories of oral iodine compositions that have been used to treat disease states in mammals: (1) organically bound iodine including both covalent binding and hydrophobic/ionic complexes, (2) inorganic iodine and (3) aqueous molecular iodine.

Organic iodine compounds, which have been used "off-label" as nutritional iodine supplements, are designed for use in the area of radiographic contrast mediums (radiopaque compounds). For instance, lymphography is used to detect and evaluate abnormalities of the lymphatic system and as a guide to surgical dissection of lymph nodes. Iodine-based radiopaque compounds are likewise employed in several different diagnostic procedures, i.e. cholecystography, myelography, urography, angiography-cholangiography. A number of different organic iodine compounds have been used for this purpose including β-(4-hydroxy-3,5-diiodophenyl)-α-phenylpropionic acid, β-(3-amino-2,4,6-triiodophenyl)-α-ethylpropionic acid, iodophenylundecylate, 3,5-diacetamido-2,4,6-triiodo-benzoate, 3,5-diacetamido-2,4,6-triiodo-benzoic acid, and ethiodized oil. The iodine atoms in these compounds are covalently bound to organic molecules. Other forms of organic iodine have been used as therapeutics including protein-bound iodine, desiccated thyroid and iodine metabolically incorporated into chicken eggs.

Inorganic iodine compositions that have been used as oral therapeutics include sodium or potassium iodide; tincture of iodine or Lugol's solution; and organic iodides that yield iodide. Aqueous compositions of these species inherently contain a very low and/or unpredictable ratio of molecular iodine to total iodine. In fact, these compositions usually contain less molecular iodine on a molar basis than other forms of iodine. For instance, Lugol's solution contains approximately 129,000 ppm of total iodine but only 170 ppm of molecular iodine or a ratio of 0.0013.

Pure aqueous solutions of molecular iodine do not exist in commerce. Molecular iodine is known to be unstable in water and this instability is a function of pH. Molecular iodine is hydrated by water and, in an aqueous system, undergoes the series of reactions shown below in equations 1 to 3.

$$I_2 + H_2O = HOI + I^- + H^+ \quad (1)$$

$$3HOI = IO_3^- + 2I^- + 3H^+ \quad (2)$$

$$I_2 + I^- = I_3^- \quad (3)$$

It is not possible to make and bottle a stable aqueous solution that contains at least a molecular iodine ratio of 0.65. For clinical applications, this limitation has previously been addressed by preparing aqueous solutions of iodine immediately prior to use and then consuming them. Elemental iodine dissolves very slowly in water. The long time necessary to dissolve elemental iodine causes the loss of some nascently formed molecular iodine due to its reaction with water as shown in equation 1 above. As a result, there are problems of consistency and ease of use with this method. Compositions that contain several different pharmacologically active agents with diverse toxicity profiles are not preferred as pharmaceutical agents.

An ideal drug produces its desired effect in all patients without causing toxic effects. The relationship between the desired and undesired effects of a drug is termed its therapeutic index or selectivity. The therapeutic index for a drug is frequently represented as the ratio of the median toxic dose to the median effective dose. In clinical studies, drug selectivity is often expressed indirectly by summarizing the pattern and nature of adverse effects produced by therapeutic doses of the drug and by indicating the proportion of patients with adverse side effects. Each separate iodine species should be considered to be a unique drug entity since they have been shown to have different oral toxicity and therapeutic index profiles. Therefore, a preferred "iodine" therapeutic is a composition wherein the all or an overwhelming majority of the total iodine atoms present are in the desired form.

The prior art demonstrates that molecular iodine is an effective therapeutic agent in a number of disease states. For instance, Eskin et al. (*Biological Trace Element Research*, Vol. 49, pp. 9–18, 1995) demonstrated that molecular iodine is "distinctly more effective in diminishing ductal hyperplasia and perilobular fibrosis in the mammary glands than iodide". The scientific literature also indicates that the oral toxicity of iodide is greater than that for molecular iodine. Another way to state this is to say that the prior art in animals and humans demonstrates that the most therapeutic form of iodine, when administered orally, is molecular iodine; also, the least toxic form of iodine when administered orally is molecular iodine. Therefore, the prior art indicates that all of the iodine in a preferred oral iodine pharmaceutical should be molecular iodine. This distinction in toxicity is especially important for a treatment regime that requires chronic dosing. As a practical matter it is acceptable to limit the potential for toxicity due to iodide to a safe range. In order to accomplish this latter objective it is necessary to limit the concentration of iodide by weight to no more than 1,000 ug/day of iodide when administered chronically and preferably it should provide no more than 150 ug/day and most preferably it should provide no more than 50 ug/day.

Since the toxicity of an oral pharmaceutical iodine drug is directly related to the ratio and concentration of the different iodine species present; the known instability of the $I_2$ species presents a challenge to the development of an oral iodine pharmaceutical composition with a preferred therapeutic index. This application describes methods to overcome the problems that exist with the prior art in the delivery of molecular iodine in an acceptable stable oral pharmaceutical.

SUMMARY OF THE INVENTION
BRIEF DESCRIPTION OF THE DRAWING

FIG. 1 shows the relationship between Molecular Iodine, Iodate and Iodine.

This application teaches a novel pharmaceutical composition for oral administration to a mammal which will convert into an effective iodine therapeutic upon contact with the stomach juices of the mammal and at a ratio of molecular iodine to total iodine of 0.65 to 1.0. This application also teaches a method for generating an effective iodine therapeutic, in situ, in the stomach of a mammal for the treatment of fibrocystic breast syndrome and other diseases that require chronic or acute dosing of therapeutic iodine. The oral pharmaceutical compositions of the present invention generate molecular iodine only upon contact with the gastric juices in the stomach of a mammal and at a pharmaceutically acceptable dosage in a ratio of molecular iodine to total iodine above at least 0.65. It should be understood that it is not presently possible to make and/or bottle a stable aqueous solution containing molecular iodine at a molecular iodine ratio relative to total iodine at or above 0.65.

Iodine sublimes at room temperature and reacts with water as previously described. These two properties make it very difficult to formulate molecular iodine; it is especially difficult to prepare compositions wherein most of the iodine exists as molecular iodine. The pharmaceutical composition of the present invention does not incorporate elemental iodine or molecular iodine in situ. The present invention provides for dramatically improved stability relative to composition that incorporate molecular iodine. Control of molecular iodine is provided by the present invention which results in generating molecular iodine at ratios of molecular iodine to total iodine between 0.65 and 1.0 and more preferably between 0.80 and 1.0 and most preferably between 0.9 and 1.0 upon contact with the gastric juices.

In accordance with the method of the present invention therapeutic iodine is administered to a mammal by feeding the mammal an effective amount of an oxidant and reductant for an iodine species which will cause oxidation-reduction reactions upon contact with the gastric juices present in the stomach of the mammal such that molecular iodine is generated, in situ, at a ratio of molecular iodine to total iodine above at least about 0.65.

The pharmaceutical composition of the present invention does not incorporate any elemental iodine or aqueous molecular iodine; the compositions described herein rely upon the environment provided by gastric fluid to initiate the formation of molecular iodine. The composition of the present invention may be provided in the form of a kit of unreacted components that react with stomach fluids to generate molecular iodine in situ. The pharmaceutical composition of the present invention can be incorporated into a single powder, capsule, tablet, caplet or liquid; in addition, combinations of these physical formats can be utilized. Oxidation and reduction reactions of different iodine species can be used to achieve this end. The principal oxidation states of iodine are −1, +1, +3, +5 and +7. Stable species in one of these oxidation states can be admixed in stomach fluids in either an oxidative or reductive environment to yield the desired iodine species which is molecular iodine.

The advantages of generating molecular iodine in situ within the stomach upon contact with the stomach fluids are: (1) production of stable, pharmaceutically acceptable composition; (2) production of a controlled dosage of molecular iodine in situ; and (3) the ratio of molecular iodine is controllable at levels above 0.65.

The methods described above allow an accurate dosage regime to be achieved and the reduction of unwanted toxic side-effects associated with iodide, triiodide and polyiodides. In addition, the therapeutic efficacy for certain disease states like fibrocystic breast syndrome is increased.

DETAILED DESCRIPTION OF THE INVENTION

Figure 1:
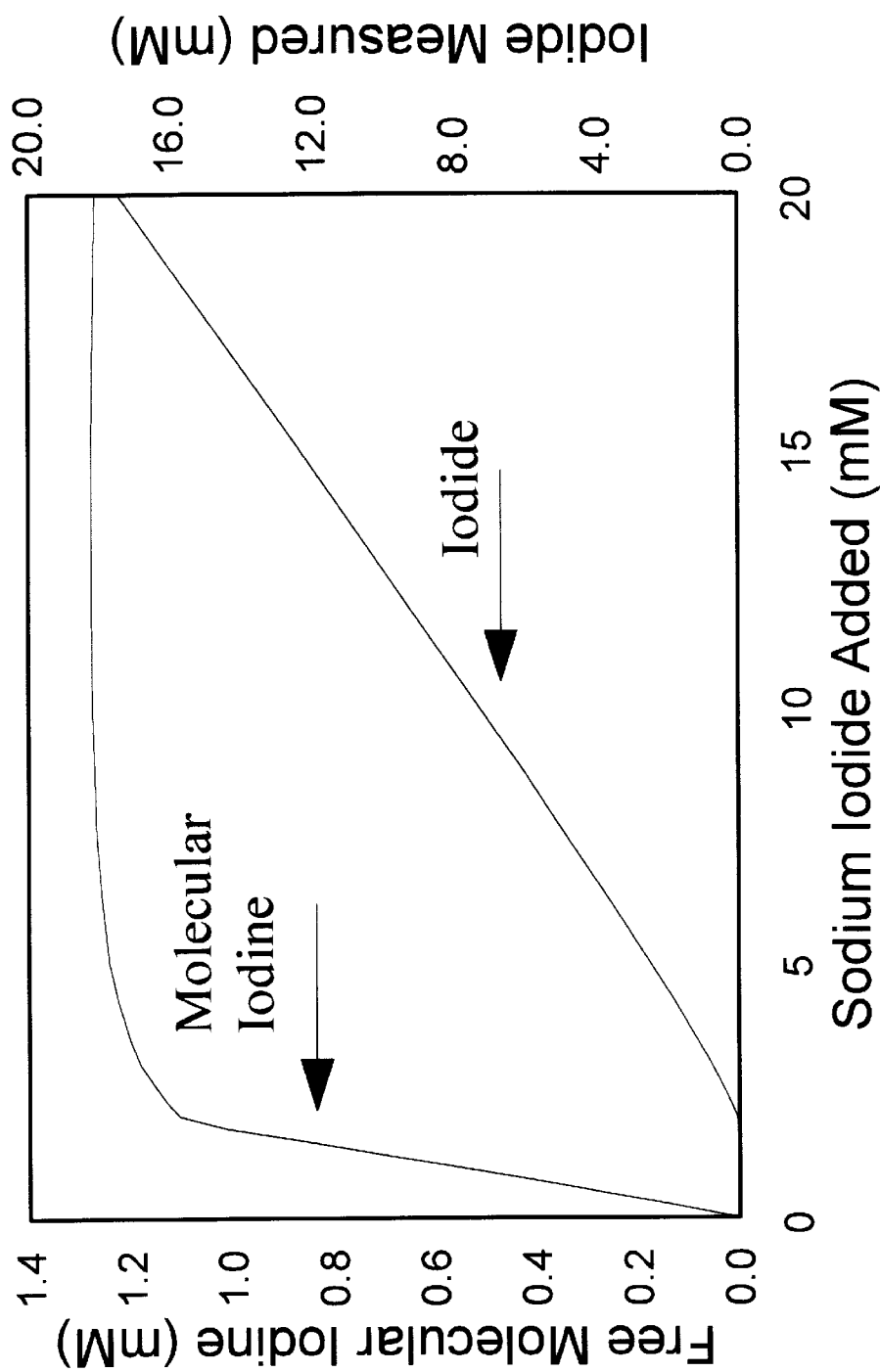

The method described in this application describes a system for the in situ generation of molecular iodine in the stomach. It is necessary to account for the composition of gastric fluid when designing such a composition. The low pH of gastric fluids influences this type of chemistry. The principal oxidation states of iodine are −1, +1, +3, +5, and +7. Compounds that are representative of these states include KI, ICl, $ICl_3$, $IF_5$, and $Na_5IO_6$, respectively. The oxide $IO_2$ is known and appears to be the sole representative of +4 oxidation state.

Molecular iodine ($I_2$) can be formed by either reducing an iodine species with a positive oxidation state or oxidizing the iodide anion ($I^-$). Alternatively, it is possible to use an oxidant and reducing agent which both contain iodine. The oxidation potentials for the different oxidation states of iodine in an acidic solution are represented below:

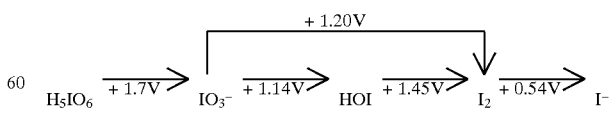

There exists a variety of iodine species in different oxidation states. The positive oxidative states are usually found in inorganic species such as acids, salts, oxides, or halides. The negative oxidative states appear in iodine species that are in the form of iodide salts or organic iodo-compounds.

The oxidation states of iodine and some iodine species that are representative of those states are shown below:

+7: periodic acid ($H_5IO_6$), potassium periodate ($KIO_4$), sodium periodate ($NaIO_4$).

+5: iodic acid ($HIO_3$), potassium iodate ($KIO_3$), potassium hydrogen iodate ($KHI_2O_6$), sodium iodate ($NaIO_3$), iodine oxide ($I_2O_5$).

+3: iodine trichloride ($ICl_3$),

+1: iodine monobromide (IBr), iodine monochloride (ICl).

−1: hydriodic acid (HI), sodium iodide, potassium iodide, ammonium iodide, aluminum iodide ($AlI_3$), boron triiodide ($BI_3$), calcium iodide ($CaI_2$), magnesium iodide ($MgI_2$), iodoform ($CHI_3$), tetaiodoethylene ($C_2I_4$), iodoacetic acid, iodoethanol, iodoacetic anhydride.

Molecular iodine can be formed from oxidation-reduction reactions according to the above indicated oxidation-reduction potentials of the half-reaction for an iodine species. Another way of stating this is as follows: substances with lower oxidation potentials can reduce an iodine species to molecular iodine and substances with a higher oxidation potential than iodide can oxidize iodide into molecular iodine. There are many chemicals known to one skilled in the art that will function in this fashion.

One desired feature of the in situ generation method is to provide a composition that is non-toxic once it has contacted gastric fluids contained in the stomach. Another parameter of this method is the speed at which molecular iodine is generated once the composition contacts gastric fluids. Another important feature of this method is to provide a reproducible quantity of molecular iodine.

Suitable oxidants for the in situ generation method include hydrogen peroxide, iodate, monopersulfate, other alkalai salts of peroxide like calcium hydroxide, peroxidases that are capable of oxidizing iodide, ascorbic acid and/or other organic acids that are generally regarded as safe.

A preferred oxidant for this invention is hydrogen peroxide. Any material that acts as a source of an oxidizing peroxy functionality when ingested is suitable for the present invention. The term "source of hydrogen peroxide" for purposes of the present invention and as used herein shall mean any material alone or in combination which is pharmaceutically acceptable to serve as a precursor for an oxidizing peroxy functionality including percarbonates, perphosphates, urea peroxide, peroxy acids, alkylperoxides, peroxyacids and perborates. Mixtures of two or more of these substances can be used.

The preferred oxidant for this invention for use in combination with the iodide anion is iodate. The iodate anion consists of one atom of iodine and three atoms of oxygen and has a negative charge associated with it at a pH of 7.0. Preferred sources of iodate include sodium iodate and potassium iodate. The term "source of iodate" for purposes of the present invention and as used herein shall mean any material alone or in combination which is pharmaceutically acceptable to serve as a precursor for the liberation or delivery of iodate upon contact with stomach fluids.

Suitable reductants for the in situ generation method include iodide, sodium thiosulfate, ascorbate, simple reducing sugars such as lactose, imidazole and other reductants well known to one skilled in the art.

The oxidant and reductant used to generate molecular iodine can be combined in a dry state with other well known pharmaceutical excipients to facilitate the manufacture of capsules, tablets and pills. Examples of such well known non-toxic excipients include: various phosphates, sucrose, lactose, maltodextrins, mannitol dextrates, dextrose, glucose, citric acid, sorbitol microcrystalline cellulose, starches, calcium carbonate, carboxymethylcellulose, polyethylene glycol boric acid, leucine, sodium chloride, benzoate, acetate, oleate, magnesium stearate, stearic acid, talc and hydrogenated vegetable oils. Other excipients will occur to one skilled in the art and are incorporated for the purposes of this application. Preferred excipients should have the following characteristics: (1) not effect the stability of the oxidant and reductant; (2) not interfere with the interaction between the oxidant and reductant; (3) not effect the yield of molecular iodine; (4) not materially react with molecular iodine in a fashion that effects the absolute concentration of molecular iodine, and (5) not effect the ratio of molecular iodine to total iodine after it is formed in the stomach and during the time which molecular iodine is processed by the mammal in the stomach or intestines.

Alternatively, it is possible to incorporate the components of the in situ generation method into a liquid that is swallowed prior to, after or contemporaneous with a powder, capsule or tablet. A variety of liquid compositions familiar to one skilled in the art are acceptable provided that the stability of the reactants to yield iodine is maintained. An example of one such liquid composition would be a suspension of powders in a viscous hydrophobic liquid such as mineral oil.

Two dosage ranges for molecular iodine are contemplated in this application; a range for chronic dosing and a range for acute dosing. Treatment of stomach ulcers which are caused by the presence of *Helicobacter pylori* in the stomach lining would be an example of a disease state that requires acute dosing. Treatment of breast displasia is an example of a disease that requires chronic dosing. The amount of molecular iodine to be provided per day for treatment of breast displasia is between 0.5 and 7.5 mg per day for a 100 pound female mammal with a preferred range of iodine for consumption between 1.0 and 5.0 mg per day. The amount of molecular iodine to be provided per day for prevention of breast displasia is between 125 ug and 0.5 mg per day for a 100 pound female mammal with a preferred range of iodine for consumption between 125 ug and 250 ug per day. The amount of molecular iodine delivered per day for acute dosing can be between 5 and 35 mg with a preferred range of iodine for consumption between 7.5 and 15 mg per day.

An important parameter of any iodine pharmaceutical is its therapeutic index. The therapeutic index for an iodine pharmaceutical is proportional to the ratio of molecular iodine to total iodine provided by said pharmaceutical. The higher the ratio of molecular iodine to total iodine, the higher the therapeutic index for the iodine composition. The ratio of molecular iodine to total iodine that is generated by iodine pharmaceuticals described in this application is between 0.65 and 1.0 with a preferred ratio of between 0.80 and 1.0 and a most preferred ratio of 0.95 and 1.0. For treatment of disease states that require chronic administration of iodine, such as fibrocystic breast syndrome, it is especially preferred to provide a composition that provides a ratio of 0.95 to 1.0. Since molecular iodine is the least toxic form of iodine, chronic administration of an oral iodine therapeutic should be based upon molecular iodine.

In order to limit toxicity from unwanted iodide it is necessary to limit the concentration of iodide (that remains after in situ generation of molecular iodine). In no event should the amount of iodide in such a composition provide more than 1,000 ug/day of iodide when administered acutely and preferably it should provide no more than 150 ug/day when administered chronically and most preferably is should provide no more than 50 ug/day. Therefore, as described in this application, the concentration of iodide in an iodine pharmaceutical for acute dosing that contains 20 mg of total iodine, should be less than 1 mg or 5% and preferably the iodide concentration should be 150 ug (or 0.75%) or less of the total weight of iodine present.

The ratio of molecular iodine to total iodine can be between 0.65 and 1.0 with a preferred ratio of between 0.80 and 1.0 and a most preferred ratio between 0.95 and 1.0. The higher the ratio of molecular iodine to total iodine, the higher the therapeutic index for the iodine composition.

The rate of iodine generation should be rapid with at least 75% of the equilibrium concentration of molecular iodine being generated within the first 10 minutes of contact between the specific iodine generating chemical agents and the stomach fluids.

The stability of the composition should be such that at least 90% of the molecular iodine generating capability remains after storage in appropriate packaging at 25° C. in relative humidity of 75% for at least 3 months and preferably 6 months. It is very important that the ratio of molecular iodine generated to total iodine does not materially change during storage. The variability of the ratio of molecular iodine to total iodine is one of the problems with some of the compositions described in the prior art.

EXAMPLES

Example 1

Total iodine was measured by thiosulfate titration as described in the United States Pharmacopeia (USP). Molecular iodine was measured by the method of Gottardi (Gottardi, W., *Fresenius Z. Anal. Chem.* Vol. 314, pp. 582–585, 1983) which relies upon measurement of the redox potential, iodide concentration and pH. Two Corning Model 345 pH meters were used in combination with a platinum reference electrode (Fisher Cat. No. 13-620-115), a Calomel electrode (Fisher Cat. No. 13-620-51) and iodide ion selective electrode (Corning Model 476127); a saturated solution of elemental iodine at 25° C. was used to calibrate the system.

Horseradish peroxidase is known to catalyze the formation of iodine in the presence of hydrogen peroxide via the oxidation of iodide. Simulated gastric fluid (SGF), as described in the USP, was prepared as follows: 2.0 grams of sodium chloride was dissolved in 750 mL of distilled water and then 7.0 mL of hydrochloric acid containing 3.2 grams of pepsin was added along with enough distilled water to bring the total volume to 1000 mL. Horseradish peroxidase (HRP) was dissolved in SGF at a concentration of 1.0 mg/mL. The activity of the horseradish peroxidase and its absorbance at 406 nm was monitored over the course of an hour. There was only a 20% decrease in the absorbance at 406 nm indicating that the tertiary structure of HRP is relatively stable in the presence of SGF. The rate at which horseradish peroxidase catalyzed the formation of iodine was correspondingly reduced at the end of the hour by approximately 33%.

Five grams of citric acid and 1 gram of sodium citrate were combined in one liter of water to yield a buffer with a pH of 3.0. A second identical buffer was prepared that contained 10% pig mucin. A mixture of two powders, sodium iodide (1 gram) and HRP (5 mg) was made, and used subsequently as a single reagent. The following reaction was initiated. Five hundred mL of buffer or five hundred mL of 10% mucin was mixed with 1.0 grams of the iodide/HRP mixture and 1.0 mL of 30% hydrogen peroxide. The concentration of molecular iodine was monitored as a function of time by the method of Gottardi. At eight minutes the buffer control had a molecular iodine concentration of 30.1 ppm; the same reaction in 10% pig mucin had a concentration of molecular iodine of 38.1 ppm.

This experiment demonstrates that a HRP can be used to catalyze the oxidation of iodide by hydrogen peroxide in the stomach and can generate molecular iodine in gastric fluid and in the presence of mucin. Additional experiments using Lugol's solution diluted in simulated gastric fluid at various ratios in the presence of 10% mucin did not yield any measurable molecular iodine. This experiments suggests that it may be advantageous to generate molecular iodine in situ in the stomach as opposed to delivering molecular iodine to the stomach.

Example 2

The effect of SGF with 10% pig mucin on three different types of iodine compositions was determined. The three different types of iodine solutions were (1) Lugol's solution diluted to deliver approximately 150 ppm of titratable iodine; (2) 10% polyvinylpyrrolidone iodine diluted to deliver approximately 150 ppm of titratable iodine; and (3) a mixture of HRP (1.5 mg/liter), sodium iodide (2 grams/liter) and hydrogen peroxide (0.08% w/v) that generates approximately 150 ppm of titratable iodine. The concentration of molecular iodine was determined potentiometrically for these three different iodine compositions in the absence and presence of 10% pig mucin and the results are shown below.

| Iodine Compositions in Simulated Gastric Fluid | | |
|---|---|---|
| | Molecular Iodine | |
| Iodine Composition | SGF | SGF + 10% mucin |
| 10% polyvinylpyrrolidone | 9 | 0 |
| Lugol's solution | 59 | 0 |
| HRP/iodide/peroxide mixture | 15 | 40 |

This experiment demonstrates that it is possible to generate significant concentrations of molecular iodine in the environment found in the stomach and that it may be preferable to generate said iodine in situ as compared to delivering iodine to the stomach in an aqueous composition.

Example 3

SGF was prepared as described in the USP and sodium iodate was dissolved in the SGF to a final concentration of 0.375 millimolar. A sequential addition of sodium iodide was made to the iodate solution. Sodium iodide was added to the iodate solution in different aliquots such that the concentration of added iodide ranged between 0.25 and 3.0 millimolar. After each addition of iodide the analytical chemistry of the resulting composition was determined.

The concentration of molecular iodine increased in a nearly linear fashion between an iodide concentration of 0.0 and 1.75 mM and then flattened out. The most obvious explanation for this observation is that once the majority of iodate had been reduced, further addition of iodide did not produce any material formation of molecular iodine. Instead of an increase in molecular iodine, the concentration of iodide increased. The concentration of sodium iodide increased in a nearly linear fashion between a sodium iodide concentration of 1.75 and 3.0 mM, while, under the identical conditions, the concentration of molecular iodine increased by less than 5%. FIG. 1 shows the results of these test. At an iodide input of 1.75 mM the concentration of molecular iodine was 1.01 mM; this is equal to about 96% of theoretical maximum yield of molecular iodine.

This experiment was repeated using 2.5 mM sodium iodate and a concentration of sodium iodide that ranged between 0 and 25 mM. The results were qualitatively identical. As iodide was added the concentration of molecular iodine increased in a linear fashion between an iodide concentration of 0 and 12.5 mM. Once the majority of iodate had been reduced, further addition of iodide did not produce any material increase in the concentration of molecular iodine. The concentration of sodium iodide increased in a nearly linear fashion between a sodium iodide concentration of 12.5 and 25.0 mM without a corresponding increase in molecular iodine. At an iodide input of 12.5 mM the concentration of molecular iodine was 7.17 mM; this is equal to 95% of theoretical maximum yield of molecular iodine.

These results indicate that it is possible to generate molecular iodine in the environment found in a human stomach in a fashion such that a material concentration of iodide does not result from the supplied chemicals. For example, when using 0.375 mM iodate and 1.75 mM sodium iodide, there was no detectable concentration of iodide while the concentration of molecular iodine was about 1.1 mM. Correspondingly, with 2.5 mM iodate and 12.5 mM iodide there was no detectable concentration of iodide while the concentration of molecular iodine was about 7.3 mM. This experiment identifies the preferred molar ratio of iodide to iodate in order to provide a composition that provides principally molecular iodine and which thereby limits the concentration of iodide. Limiting the concentration of iodide is important for disease states that require chronic dosing.

Example 4

A powder blend containing magnesium stearate, sorbitol, sodium iodide and sodium iodate was prepared. The following amounts of each material was weighed on an analytical scale (AND Company Ltd.; Model FX-3000); 25 grams of magnesium stearate; 1,000 grams of sorbitol; 55 grams of sodium iodide; and 15.75 grams of sodium iodate. Standard gelatin capsules were filled with 1 grams of the blended material and placed in screw-top wide-mouthed polyethylene bottles containing a single disposable desiccant cartridge (Fisher Cat. No. 08-594-14A). The polyethylene bottles were placed in a constant temperature environmental chamber at 40° C. in 75% relative humidity. Once a week for a three month time period, three capsules were removed, allowed to come to room temperature, and dissolved in simulated gastric fluid. The concentration of molecular iodine was determined immediately after dissolution by a potentiometric measurement. The concentration of molecular iodine did not change over a three month time period. The percentage of the concentration measured on day 1 was plotted versus time. No trend could be detected in a graph of the concentration of molecular iodine versus time.

Example 5

Soybean peroxidase (E.C. 1.11.1.7) was used in conjunction with hydrogen peroxide and iodide to generate molecular iodine in situ. The ratio of molecular iodine to total iodine was calculated. Several different reaction conditions in a citrate/carbonate buffer were established at pH values of 1.7, 4.5 and 5.0. The concentrations of the different reactants at a pH of 5.0 are shown below in tabular form.

| Reaction Conditions for Soybean peroxidase at pH 5.0 | | | |
|---|---|---|---|
| | Volume Used (ml) | | |
| | Reaction 1 | Reaction 2 | Reaction 3 |
| 0.05 molar citric acid | 16 | 16 | 16 |
| 0.1 gram/ml sodium carbonate | 8.22 | 8.2 | 8.12 |
| 30 mg/ml sodium percarbonate | 0.41 | 0.50 | 1.56 |
| 30 mg/ml sodium iodide | 0.33 | 0.40 | 1.33 |
| water | QS to 200 ml | | |

The reactions at pH 5.0 were initiated adding 0.2 ml of soybean peroxidase (5 mg/ml) and gently mixing. The concentration of molecular iodine was measured at 20 minutes by the potentiometric method of Gottardi. The concentration of molecular iodine for the three conditions at pH 5.0 was as follows: reaction 1 was 43 ppm; reaction 2 was 51 ppm and reaction 3 was 159 ppm. The ratio of molecular iodine to total iodine for the three reactions was 1.02, 1.0 and 0.94 respectively.

Another reaction was initiated at pH 4.5 using the following experimental conditions. The following chemicals were added to 1200 ml of water: 4.65 grams of citric acid, 2.0 grams of sodium carbonate, 0.252 grams of sodium iodide, 6 milligrams of lactoperoxidase (E.C. 1.11.1.7) and 80 mg of urea hydrogen peroxide. After 20 minutes the concentration of molecular iodine was determined to be 172 ppm by the potentiometric method of Gottardi. The ratio of molecular iodine to total iodine was 0.97.

Example 6

An iodine pharmaceutical must be absorbed to provide a therapeutic benefit. Ghent (U.S. Pat. Nos. 4,816,255; 5,171,582) has shown that Lugol's solution is an effective therapeutic for the treatment of fibrocystic breast syndrome. This experiment was designed to demonstrate that the bioavailability of molecular iodine generated in situ is at least equal to that of Lugol's solution.

Female Sprague-Dawley rats weighing 150–250 grams that were 6–7 weeks old were purchased from Charles River Canada, Inc. (Quebec, Canada). Rats were housed individually in stainless steel wire mesh-bottomed rodent cages equipped with an automatic watering system. Following randomization, all cages will be clearly labeled with a color-coded cage card indicating study number, group, animal number, sex and treatment. Each animal was uniquely identified by an individual ear tag following arrival. The environment was controlled at 21°±3° C., 50±20% relative humidity, 12 hours light, 12 hours dark and 10–15 air changes were made per hour. Animals were provided with Teklad (Madison, Wis.) Certified Rodent Diet (W) #8728 ad libitum. Municipal tap water that was purified by reverse osmosis and treated by ultraviolet light was provided ad libitum. The animals were allowed to acclimate to their environment for at least two weeks prior to the start of the experiment.

Rats were dosed with 1.0 ml per 250 grams for each treatment group. The concentration of iodine-based drug was either 0.1 mg/kg (the low dose "L") or 1.0 mg/kg (the high dose "H"). Different types of iodine-based drugs were dosed. Lugol's is known to be an effective treatment against fibrocystic breast syndrome and it was used as the positive control. Compositions that contained sodium iodide and sodium iodate alone, or in combination with other agents, were used as the experimental treatments. The ratio of iodide to iodate was controlled so that essentially all of the iodide was converted into molecular iodine. The experimental treatments included (1) NaI/NaIO$_3^-$ mixed prior to gavage; (2) NaI/NaIO$_3^-$ in 0.7% HCl gavaged separately; (3) NaI/NaIO$_3^-$ in 1% starch; and (4) NaI/NaIO$_3^-$ in 1% sorbitol.

Blood was drawn from animals prior to treatment. Animals were gavaged and blood was taken 2 hours later when the animals were sacrificed. The blood was processed to yield serum samples and these samples were frozen. The frozen samples were analyzed by utilizing the reduction-oxidation reaction between ceric and arsenite catalyzed by iodide. This method provides a measure of the total iodine that is absorbed in serum. The results of the these measurements are shown below in tabular form.

| Bioavailability of Iodine (ug I$^-$/dl) in Serum | | | |
|---|---|---|---|
| Treatment Group | Conc. (mg/kg) | pre-dosing | 2 hr. post-dosing |
| Lugol's | H | 9.79 | 130.6 |
|  | L | 9.50 | 20.9 |
| NaI/NaIO$_3^-$ mixed prior to gavage | H | 9.08 | 148.5 |
|  | L | 12.11 | 24.1 |
| NaI/NaIO$_3^-$ in 0.7% HCl separately gavaged | H | 9.60 | 167.3 |
|  | L | 10.8 | 30.7 |
| NaI/NaIO$_3^-$ in 1% starch | H | 9.42 | 169.8 |
| NaI/NaIO$_3^-$ in 1% sorbitol | H | 9.60 | 165.0 |

The NaI/NaIO$_3^-$ compositions were absorbed by the rats to a degree that was equivalent with or greater than Lugol's solution. This indicates that the iodine in these treatments is available to mammalian tissue.

Example 7

A seven day dosing study was conducted at different concentrations of iodine to determine the acute oral toxicity of a NaI/NaIO$_3^-$ composition. Twenty Sprague-Dawley female rats were divided into 4 groups with five animals in each group. Animals were selected and treated as described above in Example 6. Rats were dosed once each day with a NaI/NaIO$_3^-$ composition or water (control groups). The NaI/NaIO$_3^-$ composition was formulated so that essentially all of the iodine atoms were converted into molecular iodine upon use. The dose level used in the three treatment groups was (1) 0.1 mg/kg; (2) 1.0 mg/kg and (3)10 mg/kg. Each animal was dosed with approximately 2 ml per 250 grams.

During the treatment period, clinical signs (ill health, behavioral changes etc.) were evaluated at cage-side twice a day. Funduscopic and biomicroscopic examinations were performed for all animals during the pretreatment period and at the end of the treatment period. Animals were euthanized upon completion of the treatment with methoxyflurane. Necropsy examination of the carcasses was performed immediately after sacrifice.

None of the animals exhibited any clinically abnormal signs. There were no abnormal signs observed during necropsy. High doses of an iodide/iodate drug do not cause acute toxicity.

Example 8

Female Sprague-Dawley rats (a total of 44) weighing 200–250 grams were purchased from Charles River Canada, Inc. (Quebec, Canada). Rats were housed individually in stainless steel wire mesh-bottomed rodent cages equipped with an automatic watering system. The environment was controlled at 21°±3° C., 50±20% relative humidity, 12 hours light, 12 hours dark and 10–15 air changes were made per hour.

Animals were fed Remington iodine-deficient diet #170360 (Teklad, Madison, Wis.) ad libitum. Perchlorate-treated (400 mg/dL NaClO$_4$) municipal tap water was provided ad libitum for the first five days of captivity. One group of rats received a normal diet (Teklad Certified Rodent Diet (W) #8728) and municipal tap water. All animals were then allowed to acclimate to their environment for two weeks prior to the start of the experiment. Each day for the five days preceding the initiation of testing, animals received estrogen (25 ug of 17-βestradiol) suspended in 100 ul of sesame oil injected IM. During the 2 week experiment estrogen (2.5 ug 17-βestradiol) suspended in 100 ul of sesame oil was injected daily. Vaginal smears were taken every other day to insure that rats achieved constant estrus throughout the experiment.

Molecular iodine was generated in situ in the rats by gavage of an aqueous solution that contained sodium iodide and sodium iodate (5/1 molar ratio I$^-$/IO$_3^-$) such that essentially 100% of the administered iodide was converted into molecular iodine. Rats were dosed with molecular iodine once daily. Food was removed from the rats each morning and ten hours later, each rat was dosed with 80 ug/kg of molecular iodine. An equivalent dose of iodide (80 ug/kg) was given to a control group of rats. The negative control consisted of rats which were dosed with tap water. Rats were weighed daily. At the end of the 2 week study rats were sacrificed and microscopic sections of the mammary gland tissues were stained with hematoxylin and eosin prior to being read by a pathologist. Mammary tissue was scored according to the methods described by Eskin et al. (*Biological Trace Element Research*, 1995, Volume 49, pages 9–18).

Four groups of animals were examined: (1) normal diet without perchlorate treatment; (2) iodine deficient with water gavage; (3) iodine deficient with iodide gavage; and (4) iodine deficient with iodine gavage. Each group contained 10 animals. There were small but statistically significant differences in the body weights of the different groups at the start and end of the experimental treatments. However, all of the body weights were within the normal range. The average weight for the four Groups were as follows (1) 208±5.6 at start, 237±7.4 at end; (2) 212±6.3 at start, 239±6.8 at end; (3) 214±6.5 at start, 235±7.1 at end; and (4) 216±6.6 at start, 241±6.9 at end.

The mammary tissue was graded for lobular hyperplasia, secretions, periductal fibrosis, and fibroadenomatous changes. The scoring system for lobular hyperplasia, secretions, periductal fibrosis graded as positive only those animals showing moderate to severe conditions. Microscopic fibroadenomata were identified in some samples and quantified. The results of this histological grading are shown below in tabular form.

| Histologic Grading of Mammary Tissue | | | | |
|---|---|---|---|---|
| Treatment Group | Lobular hyperplasia | Secretion | Periductal fibrosis | Fibro-adenomata |
| Normal Diet | 0/10 | 0/10 | 0/10 | 0/10 |
| Iodine deficient (water gavage) | 4/10 | 2/10 | 10/10 | 3/10 |
| Iodine deficient (iodide gavage) | 4/10 | 4/10 | 6/10 | 4/10 |
| Iodine deficient (iodine gavage) | 2/10 | 3/10 | 4/10 | 1/10 |

Iodine deficiency has been shown to alter the structure and function of the mammary glands of rats, especially the alveolar cells. When stimulated by estrogen, either physiologically or externally, the mammary glands appear to be highly sensitive to iodine deprivation. The dysplasia and atypia caused by iodine deficiency in the mammary glands has been shown in extensive trials on humans to be reversible by iodine treatment. The rat model has been used by several researchers as a model of fibrocystic breast syndrome in humans. The group of rats that received the normal diet did not present any abnormal indications. The mammary tissue of the rats on the iodine deficient diet who received a water gavage showed atypical mammary tissue indicative of fibrocystic breast syndrome caused by an iodine deficiency. The iodine deficient rats who received an iodide gavage displayed increased secretion and fibroadenomata. This increase in mammary tissue secretion and mammary tissue fibroadenomata associated with iodide treatment has been previously observed in experiments by Eskin et al. (*Biological Trace Element Research,* 1995, Volume 49, pages 9–18). In contrast to iodide, gavage with the iodide/iodate mixture (i.e., iodine gavage) reduced the incidence of hyperplasia, secretion, periductal fibrosis and fibroadenoiata. This indicates that in situ generation of molecular iodine can reverse fibrocystic breast syndrome. The results of this experiment confirm that the in situ generation of molecular iodine is an effective modality for treatment of fibrocystic breast syndrome and other iodine deficiency disease states.

Example 9

A granulation incorporating iodide anion and iodate anion was prepared and its stability was evaluated at 40° C. In a Kitchen Aid mixer the following chemicals were added: 100 ml deionized water; 1.0 gram of sodium iodate; 3.63 grams of sodium iodide; 5.0 grams of tribasic sodium phosphate; and a drop of sodium hydroxide. The materials were mixed well until they were blended. Twenty five grams of hydroxypropylmethyl cellulose was added and the material was blended until it was uniform. An additional 450 grams of microcrystalline cellulose was slowly added while mixing. This granulation was passed through a number 5 sieve and then dried in a vacuum over at 50° C. After drying the material for 12 hours it was passed through a number 20 sieve.

Forty five samples of one gram of the dried granulation were weighed into glass vials and then placed in an oven at 40° C. Three samples was withdrawn approximately each week for three months and the amount of thiosulfate titratable iodine was determined after dissolution in 1 liter of simulated gastric fluid. The results of these measurements are shown below in tabular form.

Example 10

A solution of sodium iodate was prepared at a concentration of 5 millimolar in 200 ml of SGF (without pepsin) in a Teflon-lined screw-top glass bottle. A concentrated solution of ascorbic acid was added dropwise to this solution through a tube. The concentration of iodide (determined by ISE) and free molecular iodine (determined potentiometrically) was determined after each addition of ascorbic acid. The electrodes used for the iodide and free molecular iodine measurements were contacted through air-tight hole fabricated in the top of the Teflon-lined container. The concentration of molecular iodine increased in a nearly linear fashion as a function of the amount of ascorbic acid added until its concentration reached a maximum of 2.38 millimolar. After the molecular iodine reached a maximum, its concentration decreased as the concentration of ascorbic acid increased. No iodide was detected until the concentration of molecular iodine reached 2.38 millimolar. The concentration of iodide increased with increasing ascorbic acid until it reached a maximum of 4.82 millimolar at which it remained constant regardless of any increase in ascorbic acid.

The experiment was repeated using another oxidant-reductant pair. Iodate and sodium thiosulfate were substituted for iodate and ascorbic acid. The exact same experiment was repeated except that concentrated sodium thiosulfate was added dropwise to the sealed container. Once again the concentration of molecular iodine reached a maximum value of 2.26 millimolar and then decreased. As the concentration of molecular iodine decreased from its maximum value, the concentration of iodide increased from 0 to 4.7 millimolar.

Example 11

The ratio of molecular iodine to total iodine was determined as a function of the ratio of iodide anion to iodate anion in SGF (without pepsin). The following measurements were made to determine the presence of different iodine species: thiosulfate titratable iodine, potentiometric analysis of molecular iodine and ion selective electrode determination of iodide anion. It was found that essentially all of the input mass of iodine atoms was accounted for by measuring these three species. Triiodide and other polyiodides were calculated from the thiosulfate values and molecular iodine values. The ratio of molecular iodine to total iodine was determined by dividing the mass of molecular iodine by the sum of the mass of iodide, molecular iodine and triiodide.

The ratio by weight of iodide anion to iodate anion was varied from 0.5 to 8. It was observed that the ratio of molecular iodine to total iodine varied as shown in tabular form below.

Thiosulfate Titratable Iodine Generated by Iodide/Iodate Granulation versus Time at 40° C.

| Day Number | 1 | 7 | 14 | 21 | 30 | 37 | 44 | 51 | 60 | 67 | 74 | 81 | 88 | 95 |
|---|---|---|---|---|---|---|---|---|---|---|---|---|---|---|
| mg per sample | 8.7 | 8.6 | 8.7 | 8.7 | 8.8 | 8.8 | 8.7 | 8.6 | 8.7 | 8.7 | 8.6 | 8.8 | 8.7 | 8.6 |

| Ratio of Molecular Iodine to Total Iodine as a Function of the Iodide/Iodate Ratio (wt) | | | | | | | | | |
|---|---|---|---|---|---|---|---|---|---|
| Ratio iodide/iodate (wt) | 0.5 | 1 | 2 | 3 | 4 | 5 | 6 | 7 | 8 |
| Ratio molecular iodine | 0.52 | 0.72 | 0.89 | 0.97 | 0.92 | 0.76 | 0.65 | 0.56 | 0.50 |

Additional experimentation indicated that a weight ratio for the reactants, iodide and iodate, of about 0.78 ($I^-/IO_3^-$) yielded a ratio of molecular iodine to total iodine of 0.65.

Example 12

Female Sprague-Dawley rats weighing 200–250 grams were purchased from Charles River Canada, Inc. (Quebec, Canada). Rats were treated exactly as described in Example 8 and were subjected to identical procedures with respect to perchlorate and estrogen dosing.

Each rat was dosed by gavage of an aqueous solution that contained sodium iodide and sodium iodate (5/1 molar ratio $I^-/IO_3^-$) such that essentially 100% of the administered iodide and iodate was converted into molecular iodine upon contact with the stomach fluids. Rats were dosed with molecular iodine once daily. Food was removed from the rats each morning and ten hours later, each rat was dosed with one of three concentrations 0.0010, 0.010 or 0.10 mg/kg of molecular iodine. A dose of iodide (100 ug/kg) was given to a control group of rats. The negative control consisted of rats which were dosed with tap water. At the end of 4 weeks rats were sacrificed and microscopic sections of the mammary gland tissues were stained with hematoxylin and eosin prior to being read by a pathologist. Mammary tissue was scored as described in Example 8.

Six groups of animals were examined: groups 1–3 received daily doses of one of three concentrations of molecular iodine; (4) received the normal diet without perchlorate treatment; (5) received the iodine deficient diet with a water gavage; and (6) received an iodine deficient diet and were dosed with iodide (100 ug/kg). All of the rats body weights were within the normal range throughout the study. The mammary tissue was graded for lobular hyperplasia, secretions, periductal fibrosis, and fibroadenomatous changes as described in Example 8. Microscopic fibroadenomata were identified in some samples and quantified. The results of this histological grading are shown below in tabular form.

| Histologic Grading of Mammary Tissue | | | | |
|---|---|---|---|---|
| Treatment Group | Lobular hyperplasia | Secretion | Periductal fibrosis | Fibroadenomata |
| Molecular Iodine 1 ug/kg | 4.10 | 6/10 | 6/10 | 4/10 |
| Molecular Iodine 10 ug/kg | 2/10 | 4/10 | 4/10 | 1/10 |
| Molecular Iodine 100 ug/kg | 2/10 | 3/10 | 2/10 | 1/10 |
| Normal Diet | 0/10 | 0/10 | 0/10 | 0/10 |
| Water Gavage | 4/10 | 1/10 | 10/10 | 5/10 |
| Iodide Gavage | 4/10 | 5/10 | 5/10 | 3/10 |

Rats maintained on a normal diet did not exhibit clinically abnormal signs. As expected, rats on an iodine deficient diet that did not receive treatment (water gavage) presented mammary tissue whose histology is consistent with FBS. Daily treatment with iodide (100 ug/kg) did not substantially alleviate the formation of fibroadenomata. Daily treatment with molecular iodine at a concentration of 1 ug/kg did not substantially alleviate the formation of fibroadenomata and periductal fibrosis. Daily treatment with molecular iodine at a concentration of 10 and 100 ug/kg substantially reduced the formation of fibroadenomata and periductal fibrosis.

The invention is not to be construed as limited to the above examples. Other embodiments are within the scope of the following claims.

What is claimed is:

1. A method of administering therapeutic iodine for treating a disorder in a mammal comprising the steps of: feeding said mammal an effective amount of a pharmaceutically acceptable oxidant for an iodine species and a pharmaceutically acceptable iodine reductant with at least one of these compounds containing an iodine species which undergoes an oxidation-reduction reaction upon contact with the gastric juices present in the stomach of said mammal and generates molecular iodine, in vivo, at a ratio of molecular iodine to total iodine above at least about 0.65.

2. The method of claim 1, wherein said molecular iodine is generated by feeding said mammal an iodine reductant in concert with an iodine species having a positive oxidation state.

3. The method of claim 1, wherein said molecular iodine is generated by feeding said mammal an iodide oxidant and a source of an iodide anion.

4. The method of claim 2, wherein said iodine species having a positive oxidation state is selected from the group consisting of iodic acid, potassium iodate, potassium hydrogen iodate, sodium iodate, and calcium iodate.

5. The method of claim 4, wherein said iodine reductant is selected from the group consisting of iodide, sodium thiosulfate, ascorbate, lactose, reducing sugars and imidazole.

6. The method of claim 3, wherein said iodide oxidant is selected from the group consisting of hydrogen peroxide, iodate, monopersulfate, alkali salts of peroxide such as calcium peroxide, peroxidase, ascorbic acid and/or other pharmaceutically acceptable organic acids with an oxidation potential greater than −0.54 electron volts.

7. The method of claim 6, wherein said source of the iodine anion is selected from the class consisting of sodium iodide, potassium iodide, ammonium iodide, calcium iodide and magnesium iodide.

8. The method of claim 7, wherein said peroxidase is selected from the group consisting of horseradish peroxidase, soybean peroxidase, lactoperoxidase and myerloperoxidase.

9. The method of claim 1, wherein said iodine oxidant and reductant is combined with a non-aqueous pharmaceutically acceptable medium.

10. The method of claim 9, wherein said nonaqueous pharmaceutically acceptable medium is a nontoxic excipient selected from the group consisting of sucrose, lactose, maltodextrin, mannitol, dextrate, dextrose, glucose, citric acid, sorbitol, microcrystalline cellulose, starch, calcium carbonate, carboxymethylcellulose, polyethylene glycol, boric acid, benzoate, acetate, oleate, magnesium stearate, stearic acid, talc, hydrogenated vegetable oils, hydroxymethylcellulose, cellulose, sodium phosphate, sodium diphosphate, potassium phosphate and potassium diphosphate.

11. A nonaqueous composition for administering therapeutic iodine to a mammal consisting essentially of at oxidant for an iodine species, an iodine reductant wherein at least one of these compounds contains an iodine species and a non-aqueous pharmaceutically acceptable carrier with said oxidant and reductant selected to undergo oxidation-reduction reactions upon contact with the gastric juices present in the stomach of said mammal and in an amount sufficient to generate molecular iodine, in vivo, at a ratio of molecular iodine to total iodine above at least about 0.65.

12. The non aqueous composition of claim 11 wherein said oxidant is sodium iodate and wherein said reductant is sodium iodide.

13. A nonaqueous composition as defined in claim 11 wherein said oxidant and reductant comprises an iodate and an iodide respectively.

14. The composition of claim 13, wherein said iodide is selected from the group consisting of sodium iodide, potassium iodide, ammonium iodide, calcium iodide, and magnesium iodide.

15. A nonaqueous composition as defined in claim 14 wherein said iodate is selected from the class consisting of potassium iodate, sodium iodate, and calcium iodate.

16. A nonaqueous composition as defined in claim 15 wherein said non-aqueous pharmaceutically acceptable carrier is a nontoxic excipient selected from the group consisting of sucrose, lactose, maltodextrin, mannitol, dextrate, dextrose, glucose, citric acid, sorbitol, microcrystalline cellulose, starch, calcium carbonate, carboxymethylcellulose, polyethylene glycol, boric acid, benzoate, acetate, oleate, magnesium stearate, stearic acid, talc, hydrogenated vegetable oils, hydroxymethylcellulose, cellulose, sodium phosphate, sodium diphosphate, potassium phosphate and potassium diphosphate.

17. The composition of claim 13, wherein the ratio by weight of iodide anion to iodate anion ($[I^-]/[IO_3^-]$) is between 0.78 and 6.0.

18. The aqueous composition of claim 13, wherein the pH of the gastric fluid in the stomach of said mammal prior to administration of said non-aqueous composition is less than 4.5.

19. The nonaqueous composition of claim 16, wherein the iodate anion and the iodide anion are dissolved in an aqueous composition and then applied to a pharmaceutically acceptable carrier prior to drying.

20. The non-aqueous composition of claim 16, wherein said oxidant and reductant comprise a source of hydrogen peroxide, an iodide and a peroxidase selected from the group consisting of horseradish peroxidase, soybean peroxidase, lactoperoxidase and myerloperoxidase.

21. The method of claim 1, wherein the disorder to be treated is fibrocystic breast syndrome and the daily amount of iodine generated, in vivo in the stomach of the mammal is between 0.01 mg per kilogram to about 0.20 mg per kilogram of body weight of said animal.

22. The method of claim 21, wherein in the treatment of fibrocystic breast syndrome the daily amount of iodine generated, in vivo, is between 0.0025 mg per kilogram to about 0.01 mg per kilogram of body weight of said mammal.

23. The method of claim 1, wherein at least 50% of the iodine is generated in vivo within a short interval of no more than about 10 minutes from intimate contact between a composition of said oxidant and reductant with the gastric fluid in the stomach of the mamal.

24. The method of claim 23 wherein said composition further comprises a pharmaceutically acceptable carrier selected from the group consisting of sucrose, lactose, maltodextrin, mannitol, dextrate, dextrose, glucose, citric acid, sorbitol, microcrystalline cellulose, starch, calcium carbonate, carboxymethylcellulose, polyethylene glycol, boric acid, benzoate, acetate, oleate, magnesium stearate, stearic acid, talc, hydrogenated vegetable oils, hydroxymethylcellulose, cellulose, sodium phosphate, sodium diphosphate, potassium phosphate and potassium diphosphate.

25. The method of claim 1, wherein said disorder is selected from the group consisting of fibrocystic breast syndrome, breast cancer, premenstrual syndrome, endometriosis and stomach ulcers.

26. The method of claim 23, wherein said composition further comprises an inorganic or organic iodine composition.

27. The method of claim 1 wherein said oxidant is sodium iodate and wherein said reductant is sodium iodide.

28. The composition of claim 13, wherein the preferred ratio by weight of iodide anion to iodate anion is 3.63 to 1.0.

* * * * *